(12) United States Patent
Sato

(10) Patent No.: US 7,553,961 B2
(45) Date of Patent: Jun. 30, 2009

(54) METHOD OF PRODUCING A METAL PHTHALOCYANINE PIGMENT

(75) Inventor: Tadahisa Sato, Minami-ashigara (JP)

(73) Assignee: Fujifilm Corporation, Tokyo (JP)

( * ) Notice: Subject to any disclaimer, the term of this patent is extended or adjusted under 35 U.S.C. 154(b) by 661 days.

(21) Appl. No.: 11/234,130

(22) Filed: Sep. 26, 2005

(65) Prior Publication Data

US 2006/0116511 A1    Jun. 1, 2006

(30) Foreign Application Priority Data

Sep. 29, 2004    (JP) .............................. 2004-284102

(51) Int. Cl.
*C07B 47/00*    (2006.01)

(52) U.S. Cl. ...................................................... 540/145

(58) Field of Classification Search .................. 540/145
See application file for complete search history.

(56) References Cited

OTHER PUBLICATIONS

P. A. Barrett et al., "Phthalocyanines and Associated Compunds. Part XIV. Further Investigations of Metallic Derivatives." J. Chem. Soc., pp. 1157-1163 (1993).

*Primary Examiner*—James O. Wilson
*Assistant Examiner*—Paul V. Ward
(74) *Attorney, Agent, or Firm*—Birch, Stewart, Kolasch & Birch, LLP

(57) ABSTRACT

A method of producing a metal phthalocyanine pigment, which contains the step of: allowing an alkali metal salt of phthalocyanine to react with a metal salt, in a solvent which is mainly composed of a sulfur-containing aprotic polar solvent.

9 Claims, No Drawings

METHOD OF PRODUCING A METAL PHTHALOCYANINE PIGMENT

FIELD OF THE INVENTION

The present invention relates to a novel method of producing a metal phthalocyanine pigment. More specifically, the present invention relates to a method of producing a metal phthalocyanine, which includes allowing an alkali metal salt of phthalocyanine to react with a metal salt in a solvent which is mainly composed of a sulfur-containing aprotic polar solvent.

BACKGROUND OF THE INVENTION

Conventionally, phthalocyanine compounds are very useful as pigments in the field of coloring material industries, and many investigations have been conducted on such compounds for a long time. Phthalocyanine pigments can exhibit vivid color tone and high coloring (tinctorial) power, and they are widely used as cyan colorants in many fields. Examples of use applications in which the pigments are used include paints, printing inks, electrophotographic toners, ink-jet inks, and color filters. The pigments are important compounds indispensable in everyday life at the present time. Practically particularly important applications of phthalocyanine pigments as color materials (colorants), which need to have high performance in particular, include inkjet inks and color filters.

As the coloring material for ink-jet ink, dyes have been used, but they have drawbacks as to water resistance and light resistance. To overcome the drawbacks, pigments have come to be used. As cyan pigments, use may be mainly made of copper phthalocyanine pigments. Images obtained from pigment inks have remarkable advantages of superior light resistance and water resistance compared with images obtained from dye-based inks. However, the former images have the problems that the pigment is not easily formed uniformly or pulverized into fine-particles of a nanometer size, which can permeate pores in the surface of paper, and then the pigment in the image are poor in contact or adherence property to the paper.

With an increase in the number of pixels in digital cameras, there is a need for a color filter used in a CCD sensor to be made thinner. Some color filters use organic pigments (including metal phthalocyanine compounds as cyan pigments). Since the thickness of the filter depends largely on the particle diameter of the organic pigment, there has been a need to produce stable fine-particles of a nanometer-size level.

In some fields other than the field of coloring material industries, phthalocyanine compounds are used in such fields in which semiconductivity or photoconductivity of the compounds are utilized. For example, investigations have been conducted on electrophotographic photoconductors or laser printer photoconductors, based on the photoconductivity of metal-free phthalocyanines, or a variety of metal phthalocyanines, such as copper phthalocyanine, vanadyl oxyphthalocyanine, aluminum chlorophthalocyanine, zinc phthalocyanine, hydroxygallium phthalocyanine, and titanyl phthalocyanine.

Some types of metal phthalocyanines have redox power, and thus attention has focused on their application to catalysts. Since phthalocyanine compounds have multiple functions as mentioned above, not only non-metallic or copper phthalocyanines but also various types of metal phthalocyanines are increasing in importance (see "Pigment Dispersion and Stabilization and Surface Treatment Techniques and Evaluation," 2001, pp. 123-224, published by Technical Information Institute Co., Ltd., Japan; Masato Tanaka and Shouji Koma, "Phthalocyanines: Their Basic Physical Properties and Application to Functional Materials," 1991, pp. 55-124, published by Bun-Shin, Japan).

Examples of methods for producing metal phthalocyanines (e.g. copper phthalocyanine) include a method by reaction of phthalonitrile with a copper salt; a method by reaction between phthalic anhydride, a copper salt, urea, and ammonium molybdate; and a method by reaction of phthalonitrile with a copper salt in the presence of a strong organic base (W. Herbst and K. Hunger, "Industrial Organic Pigments, Production, Properties, Applications; Second Completely Revised Edition," VCH A Wiley Company, 1997, pp. 595-630).

Pigments of copper or any other transition metal phthalocyanines are hardly soluble in common solvents. Thus, it is not easy to produce a high-purity pigment, by removing by-product impurities that result from the above method. Disclosed examples of methods for producing high-purity transition metal phthalocyanines include (1) acid-paste methods, and (2) indirect synthesis methods using alkali metal phthalocyanines.

Acid-paste methods comprise the steps of: dissolving a crude reaction product in a strong acid (generally concentrated sulfuric acid), with the benefit of relatively high solubility of copper phthalocyanine or the like in a strong acid; and pouring the solution into ice water, to precipitate particles. This method can control particle size and provide a relatively high-purity product. However, the acid used in this method is highly oxidative, and thus it can produce new decomposition impurities, which can often degrade the performance of the product for use in electronic materials, catalysts, or the like, although their amount is very small.

The indirect synthesis methods using alkali metal phthalocyanines comprise the steps of: first, synthesizing an alkali metal phthalocyanine that is highly pure and relatively easy to dissolve in an organic solvent; dissolving or dispersing it in an organic solvent; and allowing it to react with a copper salt or any other transition metal salt dissolved or dispersed in an organic solvent, to precipitate a transition metal phthalocyanine. Disclosed examples of this method use either dilithium phthalocyanine or dipotassium phthalocyanine. These methods are further described in below.

Metal-free phthalocyanines are also hardly soluble compounds in organic solvents, although they have slightly better solubility in organic solvents than copper or any other transition metal phthalocyanines. When alkali metal phthalocyanines are brought into contact with a solvent with high acidity (which seems to have $pKa < \sim 17$), such as water and alcohols, they can take a proton from such a protic solvent, to form precipitates of hardly soluble metal-free phthalocyanines. Among the alkali metal phthalocyanines, however, dilithium phthalocyanine is relatively stable and soluble in absolute ethanol. In 1938, Barrett et al. reported that, based on such properties, dilithium phthalocyanine can be used in the synthesis of various transition metal phthalocyanines, through reaction with transition metal salts in absolute ethanol (P. A. Barrett, D. A. Frye, and R. P. Linstead; J. Chem. Soc., 1938, 1157).

P. A. Barrett, D. A. Frye, and R. P. Linstead (supra) also reported that dilithium phthalocyanine was "freely" soluble in ethanol. Actually, however, dilithium phthalocyanine is not very soluble, and the reaction does not proceed in a uniform solution; rather, it converts dilithium phthalocyanine dispersed in a solution into another dispersed metal phthalocyanine. In such a process, therefore, it is difficult to control the precipitation and particle size. Concerning stability, the reaction of dilithium phthalocyanine with alcohol can be suppressed when it rapidly reacts with transition metal ions in the presence of a transition metal salt. If the reaction time becomes longer because of scaling up or the like, however, the possibility of generating metal-free phthalocyanine by-products can increase.

In alcohols, dipotassium phthalocyanine is rapidly converted into metal-free phthalocyanine. In alcohols, therefore, it is not possible to perform the reaction between dipotassium phthalocyanine and a transition metal salt. In 1986, Kinoshita et al. disclosed a method in which dipotassium phthalocyanine is allowed to react with a transition metal salt in a hydroxyl-free organic solvent (JP-A-61-190562, "JP-A" means unexamined published Japanese patent application). In 1980, Wolfgang et al. disclosed a method of purifying metal-free phthalocyanine, which comprises the step of: heating dipotassium phthalocyanine together with an ether-series solvent, such as a crown ether or diethyleneglycol dimethyl ether (hereinafter referred to as "diglyme"), dimethyl sulfoxide, and dimethylformamide, so as to form a soluble complex (U.S. Pat. No. 4,197,242). Based on the disclosed method using diglyme, Kinoshita et al. found a method of synthesizing a metal phthalocyanine, which comprises the steps of: synthesizing a solution of a dipotassium phthalocyanine bis(methoxyethyl)ether complex, and allowing it to react with a transition metal salt. In this method, dipotassium phthalocyanine is uniformly dissolved in diglyme, in contrast to the case of dilithium phthalocyanine, but the transition metal salt is dispersed in diglyme during the reaction. Such a method is not sufficient for particle-size control in the synthesis of metal phthalocyanines.

In general, the methods to produce fine particles of a pigment are roughly classified into a breakdown method, in which fine particles are produced from a bulk material by pulverization or the like, and a build-up method, in which fine particles are produced by particle-growth from a gas phase or liquid phase, as described, for example, in "Experimental Chemical Lecture, 4$^{th}$ Edition," edited by the Chemical Society of Japan, vol. 12, pp. 411-488, Maruzen Co., Ltd., Japan. The pulverizing method, which has been widely used hitherto, is a fine-particle-producing method having high practicability, but it has various problems, such as that its productivity is very low in producing organic material particles of nanometer size, and that the materials to which the method can be applied are limited. In recent years, investigations have been made to produce organic material fine-particles of nanometer size by a build-up method.

In a build-up method, fine particles can be produced in a more stable manner, by allowing a dispersing agent to coexist at any time when a solution in which an organic pigment is dissolved is gradually brought into contact with an aqueous medium serving as a poor solvent for it, so that the pigment is precipitated (a so-called coprecipitation method ((a reprecipitation method)), JP-A-2003-26972). This method is effective as an easy method for producing nanometer-size particles. Under the present circumstances, however, this method cannot be applied to the synthesis of fine particles of copper or any other transition metal phthalocyanine pigments. Because for use of this method, there has been found no acceptable method to construct a copper phthalocyanine-production system that satisfies the prerequisite that the organic pigment or its precursor should be dissolved uniformly in a solvent, and that, if a reactant is present in a poor solvent, the reactant also should uniformly be dissolved in the poor solvent. Thus, there has been a demand for proposal of a system that allows the synthesis of fine particles of such a pigment as copper phthalocyanine by the reprecipitation method.

SUMMARY OF THE INVENTION

The present invention resides in a method of producing a metal phthalocyanine pigment, which comprises the step of:
allowing an alkali metal salt of phthalocyanine to react with a metal salt, in a solvent which is mainly composed of a sulfur-containing aprotic polar solvent.

Other and further features and advantages of the invention will appear more fully from the following description.

DETAILED DESCRIPTION OF THE INVENTION

According to the present invention, there is provided the following means:
(1) A method of producing a metal phthalocyanine pigment, comprising the step of:
allowing an alkali metal salt of phthalocyanine to react with a metal salt, in a solvent which is mainly composed of a sulfur-containing aprotic polar solvent;
(2) The method of producing a metal phthalocyanine pigment according to Item (1), wherein the alkali metal salt of phthalocyanine dissolved in the solvent which is mainly composed of a sulfur-containing aprotic polar organic solvent, is allowed to react with the metal salt dissolved in a solvent which is mainly composed of an aprotic polar solvent;
(3) The method of producing a metal phthalocyanine pigment according to Item (1) or (2), wherein the alkali metal salt is a sodium salt;
(4) The method of producing a metal phthalocyanine pigment according to any one of Items (1) to (3), wherein the sulfur-containing aprotic polar solvent is dimethyl sulfoxide;
(5) The method of producing a metal phthalocyanine pigment according to any one of Items (1) to (4), wherein the metal salt is a metal halide or/and a metal acetylacetonate;
(6) The method of producing a metal phthalocyanine pigment according to any one of Items (1) to (5), wherein a metal of the metal salt is a transition metal;
(7) The method of producing a metal phthalocyanine pigment according to any one of Items (1) to (6), wherein the metal salt is copper bromide;
(8) The method of producing a metal phthalocyanine pigment according to any one of Items (1) to (7), wherein one or both of a solution of the alkali metal salt of phthalocyanine dissolved in the solvent which is mainly composed of a sulfur-containing aprotic polar organic solvent and a solution of the metal salt dissolved in the solvent which is mainly composed of an aprotic polar solvent, contains at least one dispersing agent; and
(9) The method of producing according to Item (8), wherein the dispersing agent is a macromolecular dispersing agent and/or a low-molecular(-weight) dispersing agent.

The present invention is described in detail below.

To solve the above problems, after making active investigations, the inventor found that alkali metal phthalocyanines can specifically and easily be dissolved in solvents each of which is mainly composed of a sulfur-containing aprotic polar organic solvent, such as dimethyl sulfoxide, and that some types of metal salts can easily be dissolved in solvents each of which is mainly composed of an aprotic polar organic solvent, such as dimethyl sulfoxide. The inventor further found that reaction using these materials can produce copper or any other metal phthalocyanine pigments at high purity, and that, if this method is performed in the presence of a dispersing agent, fine-particle pigments can be produced. Thus, it was found that metal phthalocyanines can be produced by the reaction of a metal phthalocyanine precursor with a metal salt in a solvent which is mainly composed of a less-proton-donating organic solvent, i.e. an aprotic solvent, and that, in particular, a high-purity metal phthalocyanine pigment can be precipitated by the reaction of a uniformly dissolved metal phthalocyanine precursor with a uniformly dissolved metal salt. The present invention has been made based on these findings.

Concerning metal phthalocyanines that can be produced according to the present invention, the metal is preferably a II-, III- or IV-valent typical metal, transition metal, or inner transition metal. Examples of such metals include typical metals, such as Al, Si, Ga, Ge, As, In, Sn, Sb, Tl, and Pb; transition metals, such as Sc, Ti, V, Cr, Hn, Fe, Co, Ni, Cu, Zn, Y, Zr, Nb, Mo, Tc, Ru, Rh, Pb, Ag, Cd, La, Hf, Ta, W, Re, Os, Ir, Pt, Au, and Hg; and inner transition metals including lanthanoids and actinoids, such as Ce, Pr, Nd, Pm, Sm, Eu, Gd, Tb, Dy, Ho, Er, Tm, Yb, Lu, Th, Pa, U, Np, and Am. Transition metals are preferred, and copper (Cu) is particularly preferred, and II-valent copper is most preferred.

Phthalocyanines include unsubstituted or substituted metal-free phthalocyanines. Any substituent may be used, without being particularly limited, as long as metal phthalocyanines derived from substituted phthalocyanines having said substituent(s) can maintain the desired pigment function. The substituent is preferably an alkyl or cycloalkyl group having 1 to 6 carbon atoms, an aryl group having 6 to 10 carbon atoms, an alkoxy group having 1 to 6 carbon atoms, or a halogen atom selected from chlorine or bromine. Herein, in the present invention, any structure having a benzene ring condensed with another benzene ring(s), e.g. naphthalocyanine, is also considered as a phthalocyanine having a condensed benzene ring substituent. Unsubstituted or halogen atom-substituted metal-free phthalocyanines are preferred, and unsubstituted metal-free phthalocyanine is particularly preferred.

In the (di)alkali metal salt, the alkali metal ion is preferably ion of lithium (Li), sodium (Na), potassium (K), rubidium (Rb), or cesium (Cs), more preferably ion of Na, K, Rb, or Cs, particularly preferably sodium (Na) ion.

The metal salt includes a salt of the metal as mentions above with respect to the metal phthalocyanines. Examples of a counter anion for forming the salt include a complex-forming ligand that is not so strong to the metal, such as a halogen anion or an acetylacetonato anion. The counter anion is preferably a halogen ion selected from a chloride ion and a bromide ion, or an acetylacetonato anion, particularly preferably a bromide ion, which can form metal salts with particularly good solubility in solvents each of which is mainly composed of an aprotic polar solvent.

In the reaction of the alkali metal salt of phthalocyanine with the metal salt, the molar ratio between them, i.e. said ratio of (alkali metal salt):(metal salt), is preferably from 1:1 to 1:100, more preferably from 1:2 to 1:20.

According to the present invention, the alkali metal salt of phthalocyanine is allowed to react with the metal salt, in a solvent which is mainly composed of a sulfur-containing aprotic polar solvent. In a preferred mode, the alkali metal salt of phthalocyanine dissolved in a solvent which is mainly composed of a sulfur-containing aprotic polar organic solvent, is allowed to react with the metal salt dissolved in a solvent which is mainly composed of an aprotic polar solvent.

The sulfur-containing aprotic polar organic solvent is an organic solvent of a polarized structure having a sulfur atom(s) in the molecule. Specifically, examples of the sulfur-con- taining aprotic polar organic solvent include dimethyl sulfoxide, sulfolane, and 3-sulfolene.

Herein, in the present invention, the expression "being mainly composed of" for the solvent which contains a sulfur-containing aprotic polar solvent(s) means that said solvent consists of one or two or more of the sulfur-containing aprotic polar solvent(s), or said solvent is a mixed solvent of the sulfur-containing aprotic polar solvent(s) in combination with any other solvent(s), in which mixed solvent, the sulfur-containing aprotic polar solvent is contained in an amount of 60 mass % or more, preferably 80 mass % or more, and particularly preferably 90 mass % or more. Dimethyl sulfoxide or sulfolane is preferred, and dimethyl sulfoxide (DMSO) is particularly preferred.

Examples of the solvent that is allowed to mix with the sulfur-containing aprotic polar solvent, include aprotic solvents and protic solvents, each of which is miscible with said sulfur-containing aprotic polar solvent.

Examples of the miscible aprotic solvent include ether-series solvents, such as tetrahydrofuran, dioxane, ethylene glycol dimethyl ether (monoglyme), diethylene glycol dimethyl ether (diglyme), and triehtylene glycol dimethyl ether (triglyme); ester-series solvents, such as ethyl acetate, butyl acetate, and isobutyl acetate; ketone-series solvents, such as acetone, and methyl ethyl ketone; and amide-series solvents, such as dimethylformamide, dimethylacetamide, 2-pyrrolidone, N-methyl-2-pyrrolidone, 1,3-dimethyl-2-imidazolidinone, and tetramethyl urea. The miscible aprotic solvent is preferably an ether-series solvent or an amide-series solvent.

Examples of the miscible protic solvent include water; and alcohol-series solvents, such as methanol, ethanol, isopropyl alcohol, t-butanol, and ethylene glycol. The miscible protic solvent is preferably an alcohol-series solvent.

When the solvent to be mixed with the sulfur-containing aprotic polar solvent is an aprotic solvent, the aprotic solvent can be added as much as possible while it results in no adverse effect on the solubility of alkali metal phthalocyanine. When the solvent to be mixed with the sulfur-containing aprotic polar solvent is a protic solvent, the protic solvent may lead to a gradual conversion from alkali metal phthalocyanines to metal-free phthalocyanines, in the presence of excess of said protic solvent, although this may depend on an alkali amount present in the system. Accordingly, the protic solvent is preferably used not in excess. However, in some cases, the presence of the protic solvent may have an effect to improve the solubility of alkali metal phthalocyanine to the sulfur-containing aprotic polar solvent, and an appropriate amount of the aprotic solvent to be mixed with the sulfur-containing aprotic polar solvent can contribute toward improvement in productivity. The amount of the protic solvent that can be allowed to add to the sulfur-containing aprotic polar solvent is generally 10% or less, preferably 5% or less, particularly preferably 3% or less. Further, the amount of the aprotic solvent that can be allowed to add to the sulfur-containing aprotic polar solvent is generally 40% or less, preferably 20% or less, more preferably 10% or less.

The solvent which is mainly composed of a sulfur-containing aprotic polar solvent may be used in such an amount that the alkali metal phthalocyanine and the metal salt can be dispersed. For the purpose of simply producing the metal phthalocyanine, such an amount should be sufficient. The mass ratio of the amount of the said solvent to that of the alkali metal phthalocyanine is generally twice or more, preferably about 10 times or more. For the purpose of producing pigment fine-particles having a uniform diameter, however, the alkali metal phthalocyanine should completely be dissolved, and thus the mass ratio is preferably about 20 times or more, more preferably 40 times or more.

Use is made of the solvent which is mainly composed of an aprotic polar solvent, to dissolve the metal salt. The aprotic polar solvent is a polar solvent without a group that can easily donate a proton, such as a hydroxyl group. Specific examples of the aprotic polar solvent include ether-series solvents, such as tetrahydrofuran, dioxane, ethylene glycol dimethyl ether (monoglyme), diethylene glycol dimethyl ether (diglyme), and triehtylene glycol dimethyl ether (triglyme); ketone-series solvents, such as acetone, and methyl ethyl ketone; amide-series solvents, such as dimethylformamide, dimethylacetamide, 2-pyrrolidone, N-methyl-2-pyrrolidone, 1,3-dimethyl-2-imidazolidinone, and tetramethyl urea; and sulfur-containing solvents, such as sulfolane, dimethyl sulfoxide, and 3-sulfolene. The aprotic polar organic solvent is preferably an ether-series solvent or a sulfur-containing solvent, more preferably a sulfur-containing solvent, particularly preferably dimethyl sulfoxide.

Herein, the expression "being mainly composed of" for the solvent which contains an aprotic polar solvent(s) has the same meaning as that in the solvent which is mainly composed of a sulfur-containing aprotic polar solvent. That is, the expression "being mainly composed of" for the solvent which contains an aprotic polar solvent(s) means that said solvent consists of one or two or more of the aprotic polar solvent(s), or said solvent is a mixed solvent of the aprotic polar solvent(s) in combination with any other solvent(s), in which mixed solvent, the aprotic polar solvent is contained in an amount of 60 mass % or more, preferably 80 mass % or more, and particularly preferably 90 mass % or more.

Examples of the solvent that is allowed to mix with the aprotic polar solvent, include aprotic solvents and protic solvents, each of which is miscible with said aprotic polar solvent. The definition thereof has the same meaning as in the above solvent which is mainly composed of a sulfur-containing aprotic polar solvent, and the preferable amount of the aprotic or protic solvent that can be allowed to add to the aprotic polar solvent is also the same.

The mass ratio of the amount of the solvent which is mainly composed of an aprotic polar solvent to that of the metal salt is preferably from 1 to 20, more preferably from 5 to 10.

In order to produce stable phthalocyanine pigment fine-particles with small particle diameter, at least one dispersing agent is preferably present, in one or both of a solvent which is mainly composed of a sulfur-containing aprotic polar organic solvent (i.e. a solution) in which the alkali metal salt of phthalocyanine is dissolved, and a solvent which is mainly composed of an aprotic polar solvent (i.e. a solution) in which the metal salt is dissolved. The dispersing agent that can be used may be an anionic, cationic, amphoteric, nonionic, or pigmentary, low-molecular-weight, or macromolecular (or polymer) dispersing agent. Such dispersing agents may be used alone or in any combination of two or more of these. The low-molecular-weight dispersing agent may include a compound that is generally used as a surfactant. In the present invention, the low-molecular-weight dispersing agent has a molecular weight of 1,000 or less, and the macromolecular dispersing agent has a molecular weight (mass average molecular weight) of 5,000 or more.

Examples of the anionic dispersing agent (anionic surfactant) include acyl-methyltaurine salts, fatty acid salts, alkylsulfates, alkylbenzenesulfonates, alkylnaphthalenesulfonates, dialkylsulfosuccinates, alkylphosphates, naphthalenesulfonic acid/formalin condensates, and polyoxyethylenealkylsulfates. Acyl-methyltaurine salts are particularly preferable. These anionic dispersing agents may be used alone or in combination of two or more thereof.

Examples of the cationic dispersing agent (cationic surfactant) include quaternary ammonium salts, alkoxylated polyamines, aliphatic amine polyglycol ethers, aliphatic amines, diamines and polyamines derived from aliphatic amines and aliphatic alcohols, imidazolines derived from aliphatic acids, and salts of these cationic substances. These cationic dispersing agents may be used alone or in combination of two or more thereof.

The amphoteric dispersing agent is a dispersing agent having, in the molecule thereof, an anionic group moiety which the anionic dispersing agent has in the molecule, and a cationic group moiety which the cationic dispersing agent has in the molecule.

Examples of the nonionic dispersing agent (nonionic surfactant) include polyoxyethylene alkyl ethers, polyoxyethylene alkyl aryl ethers, polyoxyethylene fatty acid esters, sorbitan fatty acid esters, polyoxyethylenesorbitan fatty acid esters, polyoxyethylenealkylamines, and glycerin fatty acid esters. Among these, polyoxyethylenealkylaryl ethers are preferable. These nonionic dispersing agents may be used alone or in combination of two or more thereof.

The pigmentary dispersing agent is defined as a dispersing agent derived from an organic pigment as a parent material, and prepared by chemically modifying a structure of the parent material. Examples of the pigmentary dispersing agent include sugar-containing pigmentary dispersing agents, piperidyl-containing pigmentary dispersing agents, naphthalene- or perylene-derivative pigmentary dispersing agents, pigmentary dispersing agents having a functional group linked through a methylene group to a pigment parent structure, pigmentary dispersing agents (parent structure) chemically modified with a polymer, pigmentary dispersing agents having a sulfonic acid group, pigmentary dispersing agents having a sulfonamido group, pigmentary dispersing agents having an ether group, and pigmentary dispersing agents having a carboxylic acid group, carboxylic acid ester group or carboxamido group.

Specific examples of the polymer dispersing agent include polyvinyl pyrrolidone, polyvinyl alcohol, polyvinyl methyl ether, polyethylene oxide, polyethylene glycol, polypropylene glycol, polyacrylamide, vinyl alcohol/vinyl acetate copolymers, partial-formal products of polyvinyl alcohol, partial-butyral products of polyvinyl alcohol, vinylpyrrolidone/vinyl acetate copolymers, polyethylene oxide/propylene oxide block copolymers, polyacrylic acid salts, polyvinyl sulfuric acid salts, poly(4-vinylpyridine) salts, polyamides, polyallylamine salts, condensed naphthalenesulfonic acid salts, styrene/acrylic acid salt copolymers, styrene/methacrylic acid salt copolymers, acrylic acid ester/acrylic acid salt copolymers, acrylic acid ester/methacrylic acid salt copolymers, methacrylic acid ester/acrylic acid salt copolymers, methacrylic acid ester/methacrylic acid salt copolymers, styrene/itaconic acid salt copolymers, itaconic acid ester/itaconic acid salt copolymers, vinylnaphthalene/acrylic acid salt copolymers, vinylnaphthalene/methacrylic acid salt copolymers, vinylnaphthalene/itaconic acid salt copolymers, cellulose derivatives, and starch derivatives. Besides, natural polymers can be used, examples of which include alginic acid salts, gelatin, albumin, casein, gum arabic, tragacanth gum, and ligninsulfonic acid salts. Polyvinyl pyrrolidone is particularly preferable. These polymer dispersing agents may be used alone or in combination of two or more thereof.

Examples of a preferred embodiment for adding the dispersing agent to the system, include an embodiment, in which an anionic dispersing agent is incorporated in a solution of the alkali metal phthalocyanine, and a nonionic dispersing agent and/or a polymer dispersing agent are(is) incorporated in a solution of the metal salt.

The amount of the dispersing agent to be blended is preferably from 0.1 to 250 parts by mass, more preferably from 1 to 100 parts by mass, to 100 parts by mass of the pigment, to further improve uniform dispersibility and storage stability of the pigment. If the amount of the dispersing agent to be added is too small, the dispersion stability of the organic pigment fine-particles may not be improved, in some cases.

In the present invention, the two reactants (substrates) may be allowed to react in the following manner. In the process of simply producing the metal phthalocyanine pigment, the reaction can sufficiently allowed to proceed, by adding the alkali metal phthalocyanine in the form of solid, to a solution containing the metal salt dissolved or dispersed in the sulfur-containing aprotic polar solvent, followed by stirring these. However, the process of producing pigment fine-particles with high purity and a uniform diameter, preferably includes the step of: slowly adding, dropwise, a solution of the metal phthalocyanine precursor uniformly dissolved in the sulfur-containing aprotic polar solvent, to a solution of the metal salt uniformly dissolved in the aprotic polar solvent, under stirring.

The reaction temperature is generally from −20 to 200° C., preferably from 0 to 50° C., particularly preferably from 5 to 30° C.

The reaction time is generally from 1 minute to 10 hours, preferably from 10 minutes to 5 hours, particularly preferably from 30 minutes to 2 hours.

After the reaction, the resultant metal phthalocyanine may be isolated and purified, by filtration and washing. Specifically, the precipitate resulting from the reaction may be separated by filtration, washed with the same polar solvent that was utilized, then sufficiently washed with a low-boiling-point solvent capable of sufficiently being mixed with the polar solvent, such as acetone, to remove the polar solvent, followed by drying using a vacuum pump or the like. The drying may be performed under heating.

According to the present invention, there can be provided a method that can solve the problem with the conventional buildup production method and can produce high-purity metal phthalocyanine pigments and fine pigment fine-particles.

Further, according to the present invention, transition metal phthalocyanines can be synthesized at high purity free from impurities such as metal-free phthalocyanines, when an amount to be used of a solvent having a proton-donating group, such as a hydroxyl group, is limited in a given amount or less. Further, the reaction can be performed under uniform conditions at low temperatures, so that fine-particles of pigment with controlled particle diameter can be produced. These features can facilitate the production of high-purity fine metal phthalocyanine pigments, and can promise to increase the range of uses of such pigments.

The present invention will be described in more detail based on the following examples, but the invention is not intended to be limited thereto.

EXAMPLES

In the examples, a particle size distribution was measured using a dynamic light scattering particle size analyzer (Microtrack UPA150 (trade name), manufactured by Nikkiso Co., Ltd.). Measurement of a purity of metal phthalocyanine was conducted by taking a resultant metal phthalocyanine, followed by washing and then sufficiently drying, then dissolving the dried product in 95% concentrated sulfuric acid to measure UV absorption, and comparing the resultant absorbance with that of a standard at the same wavelength. Further, the presence (or absence) of any metal-free phthalocyanine was examined, by observing whether a liquid of alkaline water/DMSO in which a resultant metal phthalocyanine was added, showed any color, or not.

Reaction Liquids (A-1) to (D) for use in the examples were prepared in the following manner. The liquids each were a uniform solution. After preparation, each liquid was filtered through a 0.5 μm PTFE (polytetrafluoroethylene) microfilter before use. Abbreviations are used for the following chemical compounds: 2NaPC, disodium phthalocyanine; 2HPC, metal-free phthalocyanine; DMSO, dimethyl sulfoxide; and PVP, polyvinyl pyrrolidone.

Liquid (A-1): At room temperature, 2.5 g (4.5 mmol) of 2NaPC (manufactured by Tokyo Kasei Kogyo Co., Ltd.) was stirred and dissolved in DMSO (manufactured by Wako Pure Chemical Industries, Ltd., purity 99.0% or higher), to be 500 ml; a blue-green solution.

Liquid (A-2): 5.0 g (9.7 mmol) of 2HPC (manufactured by Tokyo Kasei Kogyo Co., Ltd.) was dissolved in DMSO, using 11.7 mL of a 1N aqueous NaOH solution, to be 500 ml; a blue-green solution containing water in about 2 mass %.

Liquid (A-3): 5.0 g (9.7 mmol) of 2HPC was dissolved in DMSO, using 7.3 g of a 28-mass % $CH_3ONa$ methanol solution, to be 500 ml; a blue-green solution containing methanol in about 1 mass %.

Liquid (B): At 100° C., 5.0 g of PVP (360,000 in mass average molecular weight, manufactured by Tokyo Kasei Kogyo Co., Ltd.) was stirred and dissolved in DMSO, to be 500 ml; a colorless transparent solution.

Liquid (C): At room temperature, 5.0 g (11.7 mmol) of sodium N-oleoyl-N-methyltaurine was stirred and dissolved in DMSO over 1 hour, to be 500 ml; a colorless transparent solution.

Liquid (D): At room temperature, 10.1 g (45.0 mmol) of $CuBr_2$ was stirred and dissolved in DMSO, to be 500 ml; a yellow solution.

Example 1

To a flask, 11 ml of Liquid (D) (the amount of $CuBr_2$, 0.99 mmol) was added, followed by stirring at room temperature. Thereto, was added, under a nitrogen stream, 0.5 g (0.90 mmol) of 2NaPC in the form of solid. After stirring for 1 hour, water was added thereto, and the resultant blue precipitate was separated by filtration, sufficiently washed with acetone, and dried, to give 0.49 g of a blue pigment. The measurement of its purity showed that it had a copper phthalocyanine content of 99.5%. Further, no presence of metal-free phthalocyanine was observed.

Comparative Example 1

To a flask, 0.22 g (0.98 mmol) of $CuBr_2$ was added, and 11 ml of diglyme was added thereto, followed by stirring at room temperature. Thereto, was added, under a nitrogen stream, 0.5 g (0.90 mmol) of PC-2Na in the form of solid. After stirring for 1 hour, water was added thereto, and the resultant blue precipitate was separated by filtration, sufficiently washed with acetone, and dried by heating under vacuum, to give 0.40 g of a blue pigment. The measurement of its purity showed that 56% of it was copper phthalocyanine and the remainder was metal-free phthalocyanine.

As shown in the above, the purity of the resultant copper phthalocyanine in Example 1 was remarkably higher than that in Comparative Example 1.

Example 2

To a flask, 0.22 g (0.98 mmol) of $CuBr_2$ was added, and 11 ml of diglyme was added thereto, followed by stirring at room temperature. Thereto, under a nitrogen stream, 100 ml of Liquid (A-1) was added, dropwise, slowly (over about 30 minute). After the dropwise addition was completed, stirring was performed for 30 minutes. Water was added thereto, and the resultant blue precipitate was separated by filtration, sufficiently washed with acetone, and dried by heating under vacuum, to give 0.49 g of a blue pigment. The measurement of its purity showed that it had a copper phthalocyanine content of 99.4%. Further, no metal-free phthalocyanine was observed.

Comparative Example 2

To a flask, 0.5 g (0.90 mmol) of PC-2Na was added, and under a nitrogen stream, 100 ml of diglyme was added thereto, followed by heating under stirring at 80°C. for 1 hour. After the temperature was lowered to room temperature, impurities were separated by filtration, and the resultant filtrate solution was added to a solution of 0.22 g (0.98 mmol) of $CuBr_2$ and 11 ml of diglyme under stirring, at room temperature. After stirring for 1 hour, water was added thereto, and the resultant blue precipitate was separated by filtration, sufficiently washed with acetone, and dried by heating under vacuum, to give 0.2 g of a blue pigment. The measurement of its purity showed that it had a copper phthalocyanine content of 97.0%. Further, a few presence of metal-free phthalocyanine could be observed.

As shown in the above, the blue pigment yield of Example 2 was about 2.5 times that of Comparative Example 2, and the purity of the copper phthalocyanine was much higher in Example 2 than in Comparative Example 2.

Example 3

To a flask, 10 ml of Liquid (D) (the amount of $CuBr_2$, 0.20 g (0.90 mmol)) was added, and thereto, under a nitrogen stream, 100 ml of Liquid (A-1) (the amount of PC-Na, 0.50 g (0.90 mmol)) was added, dropwise, under stirring at room temperature over about 1 hour. As the Liquid (A) was added dropwise, an insoluble blue product was generated, to form a precipitate gradually. After the dropwise addition was completed, water was added, and the precipitate was separated by filtration, sufficiently washed with acetone, dried by heating under vacuum, to give 0.51 g of a blue pigment. The measurement of its purity showed that it had a copper phthalocyanine content of 99.8%. Further, no presence of metal-free phthalocyanine was observed.

Example 4

To a flask, 20 ml of Liquid (B) and 10 ml of Liquid (D) were added, followed by stirring under a nitrogen stream at room temperature. Using a syringe pump, thereto, 10 ml of Liquid (A-1) was added, dropwise, over 1 hour. The resultant precipitate was separated by a 0.1 μm PTFE filter. The resultant filtrate was a pale yellow DMSO layer, and no contaminant of the blue compound was observed. The resultant blue product and the PTFE filter to which the product adhered were placed in a flask, and 100 ml of an aqueous 1.0-mass % sodium N-oleoyl-N-methyltaurine solution was added thereto. After ultrasonic wave was applied thereto for 10 minutes (using a 30 W ultrasonic cleaner with oscillation frequency 45 kHz), stirring was performed for 1 hour with a stirrer. The resultant liquid was allowed to pass through a 0.45 μm CE filter so that almost all blue matter was transferred to the filtrate with an extremely small amount of matters separated. The diameters of the particles in the filtrate were measured, and their median average particle diameter was 78.2 nm (number distribution). In order to determine the purity of the resultant water-soluble pigment fine-particles, part of the blue material obtained by filtration with a 0.1 μm PTFE filter was dissolved in concentrated sulfuric acid, followed by measurement of UV absorption. As a result, it was showed that almost all the pigment was only copper phthalocyanine. Further, after exposing the resultant pigment product to alkaline water/DMSO, no presence of metal-free phthalocyanine was observed.

Example 5

To a flask, 20 ml of Liquid (B) and 10 ml of Liquid (D) were added, followed by stirring to mix these each other, under a nitrogen stream at room temperature. Using a syringe pump, thereto, a mixture solution of 10 ml of Liquid (A-1) and 10 ml of Liquid (C) was added dropwise, over 1 hour. The resultant precipitate was separated by a 0.1 μm PTFE filter. The resultant filtrate was a pale yellow DMSO layer, and no contaminant of the blue compound was observed. The resultant blue product and the PTFE filter to which the product adhered were placed in a flask, and 100 ml of an aqueous 1.0-mass % sodium N-oleoyl-N-methyltaurine solution was added thereto. After ultrasonic wave was applied thereto for 10 minutes (using a 30 W ultrasonic cleaner with oscillation frequency 45 kHz), stirring was performed for 1 hour with a stirrer. The resultant liquid was allowed to pass through a 0.45 μm CE filter so that almost all blue matter was transferred to the filtrate with an extremely small amount of matters separated. The diameters of the particles in the filtrate were measured, and their median average particle diameter was 76.8 nm (number distribution). The purity of the resultant pigment fine-particles was examined in the same manner as in Example 4. As a result, almost all the pigment was copper phthalocyanine, and similar to the above no presence of metal-free phthalocyanine was observed.

Comparative Example 3

Synthesis of pigment fine-particles was tried using the process of Example 4 or 5, except that the reaction was performed in any other aprotic polar solvent, e.g. diglyme. While $CuBr_2$ was soluble in diglyme, PC-Na, PVP, and sodium N-oleoyl-N-methyltaurine each had a conspicuously lower solubility in diglyme than in DMSO, as a result, it was impossible to construct an evaluative practical system for room temperature reaction.

Example 6

The pigment dispersion (filtrate) was obtained in the same manner as in Example 5, except that Liquid (A-1) was replaced with Liquid (A-2) in the same amount. The diameters of the particles in the resultant filtrate were measured, and their median average particle diameter was 77.6 nm (number distribution). The purity of the resultant pigment fine-particles was examined in the same manner as in Example 4. As a result, almost all the pigment was copper phthalocyanine, and similar to the above no presence of metal-free phthalocyanine was observed.

Example 7

The pigment dispersion (filtrate) was obtained in the same manner as in Example 5, except that Liquid (A-1) was replaced with Liquid (A-3) in the same amount. The diameters of the particles in the resultant filtrate were measured, and their median average particle diameter was 76.1 nm (number distribution). The purity of the resultant pigment fine-particles was examined in the same manner as in Example 4. As a result, almost all the pigment was copper phthalocyanine, and similar to the above no presence of metal-free phthalocyanine was observed.

Comparative Example 4

The pigment dispersion (filtrate) was obtained in the same manner as in Example 7, except that Liquid (A-3) was replaced with a liquid prepared by adding 1.5 mL of methanol to Liquid (A-3) in the same amount, which liquid contained methanol in 10 mass % or more. The diameters of the particles in the resultant filtrate were measured, and their median average particle diameter was 78.1 nm (number distribution). The purity of the resultant pigment fine-particles was examined in the same manner as in Example 4. As a result, however, it was confirmed that the content of copper phthalocyanine was low, and that fine particles of metal-free phthalocyanine in an amount that was not negligible was introduced.

As can be seen from a comparison between the Examples 6 and 7 and the Comparative Example 4, it is apparent that metal-free phthalocyanine is formed in the presence of an excess protic solvent, which is a problem; but that copper phthalocyanine high in purity can be synthesized, while almost no metal-free phthalocyanine is formed, when the protic solvent is used in a given amount or less.

Having described my invention as related to the present embodiments, it is my intention that the invention not be limited by any of the details of the description, unless otherwise specified, but rather be construed broadly within its spirit and scope as set out in the accompanying claims.

What I claim is:

1. A method of producing a metal phthalocyanine pigment, comprising the step of:

reacting an alkali metal salt of phthalocyanine with a metal salt, wherein the alkali metal salt of phtalocyanine is dissolved in a solvent comprising a sulfur-containing aprotic polar solvent.

2. The method of producing a metal phthalocyanine pigment according to claim 1, wherein the alkali metal salt of phthalocyanine dissolved in the solvent comprising a sulfur-containing aprotic polar organic solvent is reacted with the metal salt dissolved in a solvent comprising an aprotic polar solvent.

3. The method of producing a metal phthalocyanine pigment according to claim 1, wherein the alkali metal salt is a sodium salt.

4. The method of producing a metal phthalocyanine pigment according to claim 1, wherein the sulfur-containing aprotic polar solvent is dimethyl sulfoxide.

5. The method of producing a metal phthalocyanine pigment according to claim 1, wherein the metal salt is at least one selected from the group consisting of a metal halide and a metal acetylacetonate.

6. The method of producing a metal phthalocyanine pigment according to claim 1, wherein a metal of the metal salt is a transition metal.

7. The method of producing a metal phthalocyanine pigment according to claim 1, wherein the metal salt is copper bromide.

8. The method of producing a metal phthalocyanine pigment according to claim 1, wherein at least one solution selected from the group consisting of a solution of the alkali metal salt of phthalocyanine dissolved in the solvent comprising a sulfur-containing aprotic polar organic solvent and a solution of the metal salt dissolved in a solvent comprising an aprotic polar solvent further comprises at least one dispersing agent.

9. The method of producing according to claim 8, wherein the dispersing agent is at least one selected from the group consisting of a macromolecular dispersing agent and a low-molecular-weight dispersing agent.

* * * * *